United States Patent [19]

Lousig-Nont

[11] 4,358,279
[45] Nov. 9, 1982

[54] HONESTY TESTING AND SCORING EVALUATOR

[76] Inventor: Gregory M. Lousig-Nont, 9325 Grimm La., Edwards, Ill. 61528

[21] Appl. No.: 293,492

[22] Filed: Aug. 17, 1981

[51] Int. Cl.³ .......................................... G09B 19/00
[52] U.S. Cl. .................................................. 434/363
[58] Field of Search ............................... 434/326, 363

[56] References Cited

U.S. PATENT DOCUMENTS

| | | | |
|---|---|---|---|
| 2,614,338 | 10/1952 | Clark | 434/363 |
| 2,977,689 | 4/1961 | Rugland et al. | 434/363 X |
| 3,086,300 | 4/1963 | Rugland et al. | 434/363 X |
| 3,280,483 | 10/1966 | Davenport | 434/326 |
| 3,372,494 | 3/1968 | Marcus | 434/363 |
| 3,789,520 | 2/1974 | Lowi | 434/363 |
| 4,175,339 | 11/1979 | Jones | 434/326 |

*Primary Examiner*—William H. Grieb
*Attorney, Agent, or Firm*—McCaleb, Lucas & Brugman

[57] ABSTRACT

An honesty testing and scoring evaluator comprising a questionaire, an answer and score sheet set, and a tally sheet. The questionaire has numbered interrogatories with optional answers alongside each. The answer and score sheet set includes an answer sheet overlying a score sheet. A coating on the back of the answer sheet transfers a mark, placed on it, to the score sheet. The answer sheet has numbered areas corresponding to the numbered interrogatories on the questionnaire, and each of these areas has circled marking spaces corresponding to the optional answers alongside the respective interrogatories. The score sheet has numbered areas which register with like-numbered areas on the answer sheet. The score sheet has a variety of different-shaped symbols, at least one of which is in exact registration with at least one of the marking circles on the answer sheet. In the example shown, these symbols are provided with five different shapes. One shape is for honest attitude answers. The other shapes are for different degrees of dishonest attitude answers ranging from minor to major admissions of dishonesty. The tally sheet assigns a predetermined numerical value to each honest attitude symbol marked, and assigns a different multiple of that predetermined value to each different dishonest attitude symbol marked, and provides a sequence for deriving a single numerical total score evaluating honesty of an individual marking the answer sheet.

10 Claims, 6 Drawing Figures

Fig. 1

PAGE A

| | | |
|---|---|---|
| 1. | The average person will usually steal if they think that they won't get caught. | TRUE FALSE 1. |
| 2. | Most of the time people who get involved in stealing are just victims of circumstance. | TRUE FALSE 2. |
| 3. | People who steal, probably have some kind of mental problem. | TRUE FALSE 3. |
| 4. | Most people will do something dishonest, if the price is right. | TRUE FALSE 4. |
| 5. | There are times when the temptation to steal something becomes so strong, that no average human-being could resist. | TRUE FALSE 5. |
| 6. | There is no one who can honestly say that they have not stolen something from a place where they have worked. | TRUE FALSE 6. |
| 7. | The only reason everybody doesn't steal is because some people are too scared they would get caught. | TRUE FALSE 7. |
| 8. | A basically honest person, can sometimes get talked into stealing from a place where they work, by someone who is dishonest. | TRUE FALSE 8. |
| 9. | I'm too scared I'd get caught stealing, that's the only reason I don't. | TRUE FALSE 9. |
| 10. | I tried to steal something before, but I decided not to. | TRUE FALSE 10. |
| 11. | I have at times planned to steal something, but I didn't go through with it. | TRUE FALSE 11. |
| 12. | I have gotten some really rotten breaks in life. | TRUE FALSE 12. |
| 13. | I think a certain degree of dishonesty is just part of human nature. | TRUE FALSE 13. |
| 14. | If I had to take a lie-detector test to show that I had not been involved in stealing from a place where I worked, I would not tell anybody I was going to take the test. | TRUE FALSE 14. |
| 15. | If I had a dollar for every time I thought about stealing something, I'd be a rich person. | TRUE FALSE 15. |
| 16. | If a package that belonged to your neighbor arrived at your house by mistake, would you open it just to see what was inside? | YES NO 16. |

PAGE J

97. If you were to total the amount of cash (paper money and coins) that you have taken, (stolen) from all of the places where you have worked, what would be the total amount? (MARK ONLY ONE!) NO MORE THAN;

a. $5,000.
b. $1,000.
c. $ 500.
d. $ 250.
e. $ 100.
f. $ 50.
g. $ 25.
h. $ 10.
i. $ 5.
j. $ 1.
k. $ 0.
l. I HAVE NEVER HAD A JOB BEFORE

98. If you were to total the amount of cash (paper money and coins) that you have taken, (stolen) in just the last 2 years, from places where you have worked, what would be the total amount? (MARK ONLY ONE!) NO MORE THAN;

a. $3,000.
b. $1,000.
c. $ 500.
d. $ 250.
e. $ 100.
f. $ 50.
g. $ 25.
h. $ 10.
i. $ 5.
j. $ 1.
k. $ 0.
l. I HAVE NEVER HAD A JOB BEFORE

99. Other than from jobs, what would you estimate would be the total amount of money that you have taken, (stolen) without permission from other places, such as school, parents, friends? (MARK ONLY ONE!) NO MORE THAN;

Tally Sheet

110

NAME: _____

RESULTS;    Numbers inside ( ) indicate total possible;

TOTAL ALL MARKS INSIDE;    (51)   120 ◯

HONEST ATTITUDE ANSWERS    + 150

SUB-TOTAL = ⎫ 136

126 Count all marks inside;   138

RATIONALIZES DISHONESTY AND THINKS ABOUT STEALING   (18) △   X 4 = ............(-   )

Count all marks inside;   140

BAD ATTITUDE ANSWERS   (32) □   X 3 = ............(-   )

124 Count all marks inside;   142

MINOR ADMISSIONS OF DISHONESTY   ( 7) ⌒   X 2 = ............(-   )

122 Count all marks inside;   144

MAJOR ADMISSIONS OF DISHONESTY   (21) ⌂   X 5 = ............(-   )

128

ADD NEGATIVE TOTAL = (-   ) 146   148 and subtract from sub-total above........(-   )

TOTAL SCORE; = _____

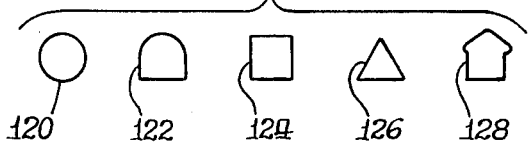

120   122   124   126   128

HONESTY TESTING AND SCORING EVALUATOR

BACKGROUND OF THE INVENTION

This invention relates to an honesty testing and scoring evaluator. More specifically, it relates to an honesty attitude test consisting of printed materials which are quick and easy to use, and provide a reliable and accurate evaluation of an individual's attitude toward honesty.

A major problem of managing a retail business is obtaining honest and conscientious employees. The American Management Association has estimated that American businesses lose ten billion dollars a year to employee theft, five times the amount lost to shoplifters. The National Retail Merchants' Association has reported merchandise shortages cost retailers sixteen million dollars every day. Pre-employment polygraph screening of prospective employees is very effective, but requires the use of sophisticated electronic equipment operated by an expert who is thoroughly trained in polygraph techniques. Only one prospect can be screened at a time, so polygraph testing is not practical where large numbers of job applicants have to be screened, especially in locations where polygraph experts are not readily available.

SUMMARY OF THE INVENTION

Accordingly, a principal object of the present invention is to provide an honesty testing and scoring evaluator in the form of a printed questionnaire and related materials which are effective and inexpensive and which can be used routinely by employers on their own premises to screen a single job applicant, or several at the same time, without the personal supervision of a polygraph operator or a deception expert.

Another object is to provide an honesty testing and scoring evaluator which consists of a printed questionnaire having numbered interrogatories requiring true-false, multiple choice, matching, or fill-in answers, and a two-page answer and score sheet set consisting of an answer sheet and a score sheet with means between the sheets for transferring to the score sheet a mark made on the answer sheet, the score sheet having symbols registered with answer marking areas on the answer sheet, the symbols having a distinctive shape for honest attitude answers and a plurality of different distinctive shapes for dishonest attitude answers indicating different degrees of dishonest attitudes.

Another object is to provide, in such a testing and scoring evaluator, a tally sheet having a procedure for grading the symbols marked on the score sheet by assigning a predetermined numerical value to honest attitude symbols and assigning multiples of that predetermined numerical value to the dishonest attitude symbols, and combining those numerical values to derive a single numerical total score evaluating whether an individual has an acceptable, a marginal, or a poor attitude toward honesty.

BRIEF DESCRIPTION OF THE DRAWINGS

Other objects and advantages will be apparent from the following description taken in connection with the drawings in which:

FIG. 1 is a plan view of a specimen page from a multi-page questionnaire employed in the present invention;

FIG. 2 is plan view of another specimen page from the questionnaire;

FIG. 3 is a plan view of an answer sheet portion of an answer and score sheet employed in the present invention;

FIG. 4 is a plan view of a score sheet portion of the answer and score sheet set;

FIG. 5 is a plan view of a tally sheet; and

FIG. 6 are honesty-dishonesty evaluation symbols employed on the score sheet.

Like parts are referred to by like reference characters.

DETAILED DESCRIPTION OF THE PREFERRED EMBODIMENT

Figure 3:
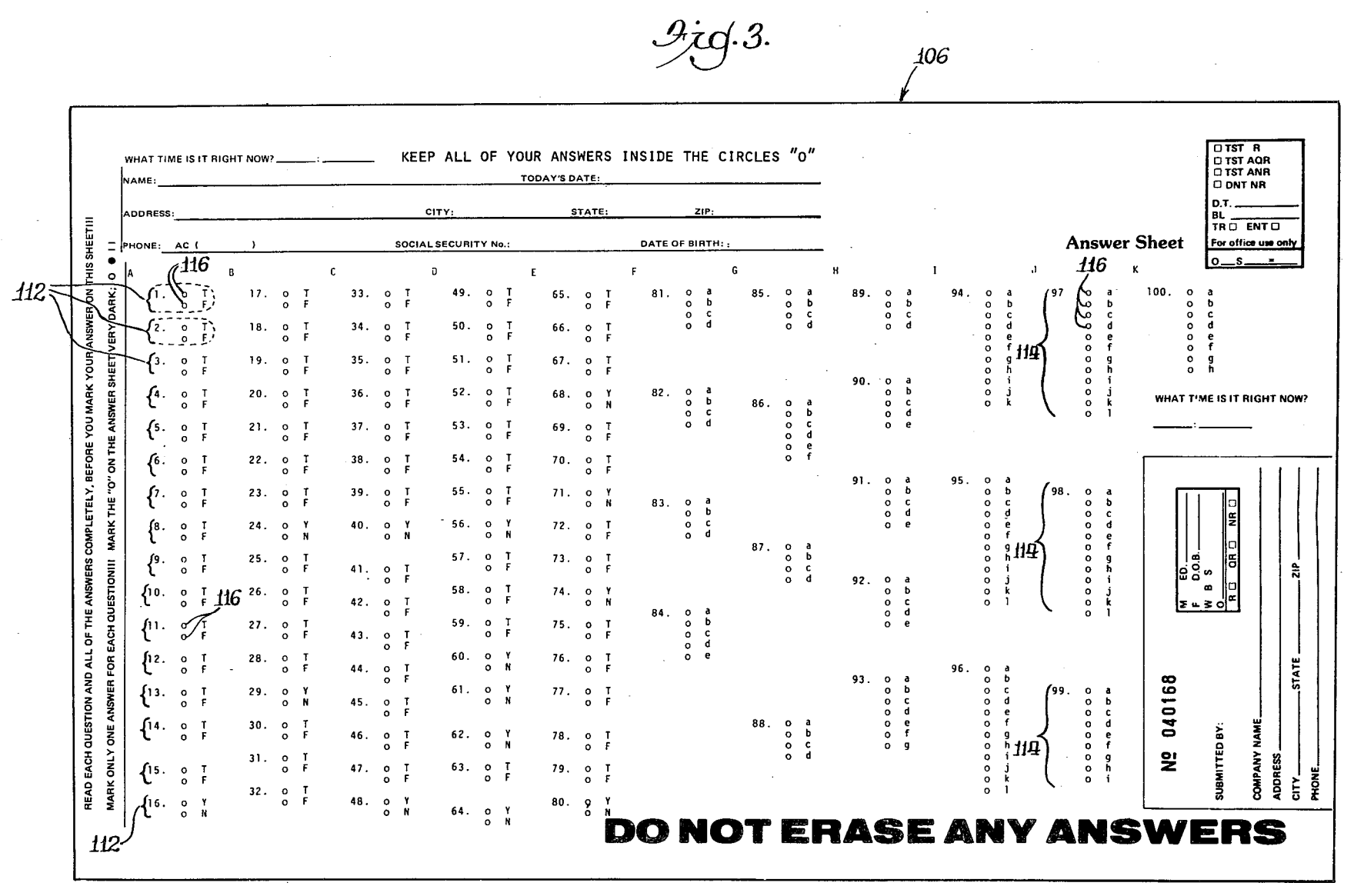
Figure 4:
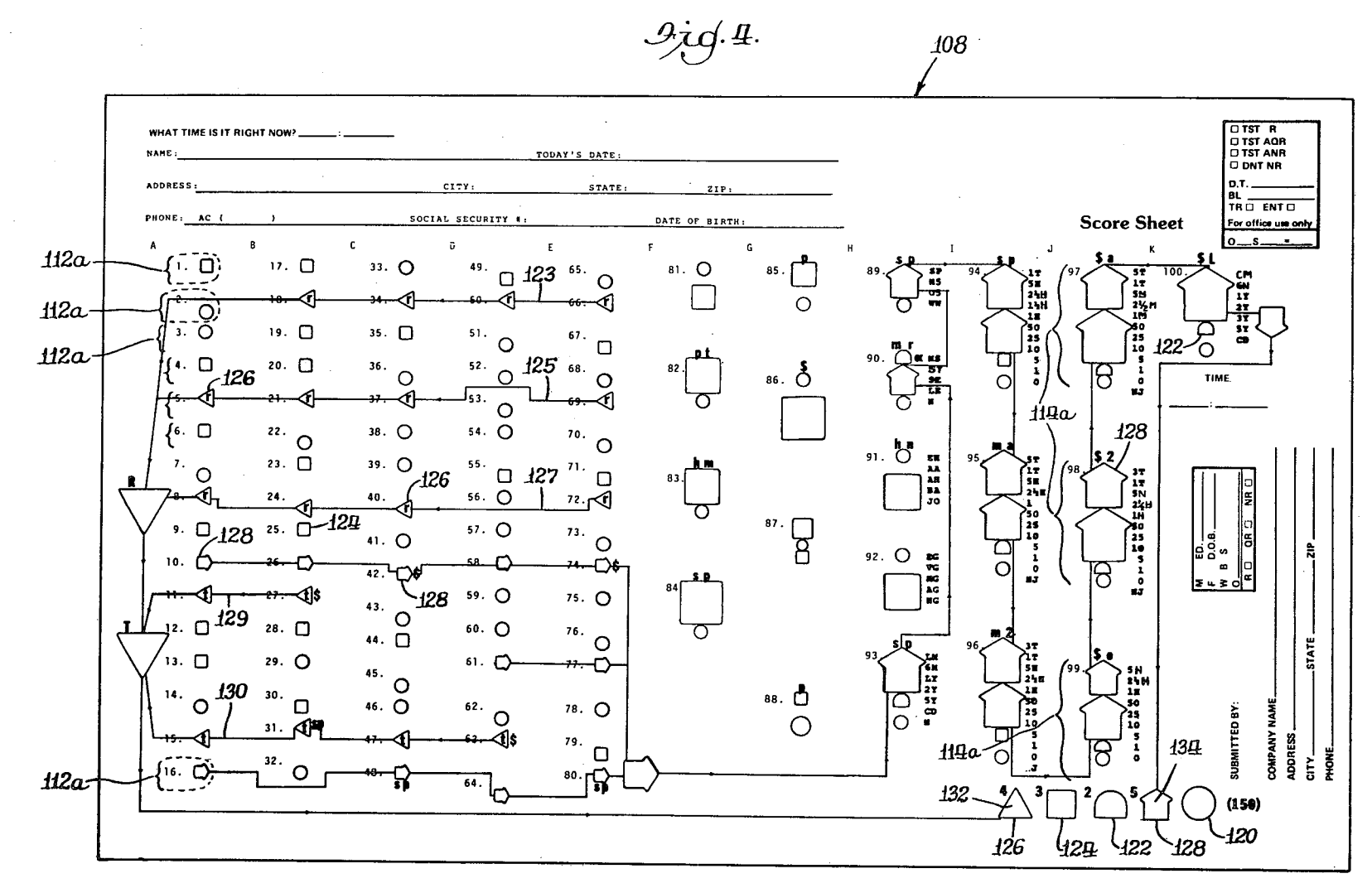

The invention comprises a questionnaire (not shown) which may be in booklet form having several pages. Two specimen pages 102 and 104 from such a questionnaire booklet are illustrated in FIGS. 1 and 2. In addition, the invention comprises a question and answer set consisting of an answer sheet 106 shown in FIG. 3 and a score sheet 108 shown in FIG. 4. A tally sheet 110 shown in FIG. 5 provides means for grading the answers marked on the score sheet symbols and means for deriving a single numerical honesty-dishonesty total score as will be explained.

In one example of the present invention, the questionnaire comprises eleven pages identified as pages A through K. Only pages A and J, shown in FIGS. 1 and 2, are specifically illustrated here, these being typical. Each of the questionnaire pages has a plurality of numbered interrogatories with a plurality of optional answers printed alongside each. On page 102, the interrogatories are sixteen statements, fifteen calling for true or false answers and one calling for yes or no answers. On page 104, the interrogatories are three questions with multiple choice answers. Other forms of interrogatories may require matching of indicia, filling in of blanks, or punching holes through the answer and score sheets. The exact type of interrogatories and kinds of answers are not critical to the practice of this invention.

Answer sheet 106 has eleven columns A through K, corresponding to the above-mentioned pages A through K in the questionnaire booklet. Each column on the answer sheet has a plurality of numbered areas 112 corresponding to the plurality of numbered interrogatories on the corresponding questionnaire page. For example, page 102 has sixteen interrogatories and there are sixteen correspondingly numbered areas 112 in column A on answer sheet 106. Likewise, page 104 has three interrogatories and there are three correspondingly numbered areas 114 in column J on the answer sheet.

The answer sheet has three items in each of the numbered areas 112 and 114. In column A, these are: the interrogatory number; a pair of optional marking circles 116; and the letters "T and F" (or "Y and N", in one case). The letters "T and F" correspond to "True and False" and the letters "Y and N" correspond to "Yes and No" on questionnaire page 102. Similarly, areas 114 on the answer sheet comprise three items; the interrogatory number; a relatively large number of marking circles 116 corresponding to each of the multiple choices for the answer; and letters a, b, etc. identifying the individual multiple choices.

Means is provided between the answer and score sheets to transfer to the score sheet any mark made in the marking circles 116 on the answer sheet. This is not specifically shown on the drawings but one such means which has been found to be satisfactory is referred to in the stationary trade as "NCR coated paper" in which a coating is placed on the back of the answer sheet and is transferable to the score sheet by pressure on the front of the answer sheet. Alternatively, carbon paper inserted between the sheets may be used.

Score sheet 108 is exactly the same size as answer sheet 106. During a test, the score sheet is semipermanently attached to the back of the answer sheet so as to be out of sight to the individual while being tested and is removed later by the person authorized to score the test and evaluate the results afterward. The score sheet has a plurality of numbered areas 112a and 114a exactly registering and corresponding with areas 112 and 114 respectively on the answer sheet.

The score sheet 108 has two items in each area (exemplified by areas 112a and 114a) corresponding to one of the numbered interrogatories. One of these items is the interrogatory numeral which is in exact registration with the same numeral on the answer sheet 106. The other item is one or more hollow symbols taken from a group of symbols having different predetermined shape.

The group of symbols is generally designated 188 (FIG. 6) and consists of: a circle symbol 120; a tombstone symbol 122; a square symbol 124; a triangle symbol 126; and an arrow symbol 128. As will be described, an important feature of the invention, in closely approximating honesty evaluation scores from polygraph testing, is assigning a predetermined numerical honesty rating to the circle symbols 120 and numerical dishonesty ratings to the symbols 122-128 which vary according to the degree of dishonesty indicated by an answer.

One or more of the symbols 120-128 are printed on score sheet 108 in registration with one or more of the marking circles 116 in each answer set on answer sheet 106. Some specific examples follow.

If the first interrogatory, "The average person will usually steal if they think that they won't get caught.", is answered as true, the upper one of the marking circles 116 for interrogatory 1 is marked on the answer sheet. The mark is transferred to the square symbol 124. As will be described, this is an indication of dishonesty with a rating of minus three points.

Referring to the second interrogatory, "Most of the time people who get involved in stealing are just victims of circumstance.", if its is answered as false, the lower one of the pair of marking circles is marked on the answer sheet. The mark is transferred to the circle symbol 120 on the score sheet and gets an honest rating.

Referring to the fifth interrogatory, "There are times when the temptation to steal something becomes so strong, that no average human being could resist.", if this is answered as true, the upper one of the pair of marking circles is marked on the answer sheet. The mark is transferred to the triangle symbol 126 and gets a dishonest rating of minus four points.

If the tenth interrogatory, "I tried to steal something before, but I decided not to.", is answered true, a mark appears on arrow symbol 128 which comprises a major admission dishonesty with a rating of minus five points.

If the ninety-eighth interrogatory regarding the total amount of cash stolen in the last two years is marked for any of the denominations from five dollars up to three thousand dollars, a mark will appear in one of the arrow symbol 128, 128 on the score sheet. This is a major indication of dishonesty with a rating of minus five points. On the other hand, if the amount admitted stolen is only one dollar, the mark will appear in the tombstone symbol 122 on the score sheet and this will have a dishonesty rating of only minus two points.

The circle symbols 120 represent attitudes that applicant has found statistically indicate a very good attitude regarding honesty. For purposes of deriving the total score, these are assigned a predetermined numerical value of plus one.

Tombstone symbols 122 represent admissions of a nature, or acts of dishonesty that occurred some time ago. These are considered minor admissions of dishonesty and are rated minus two.

Square symbols 124 represent attitudes that applicant has found statistically indicate a very bad attitude with respect to honesty. They are rated minus three.

Triangle symbols 126 deal with two different kinds of dishonesty which the arrangement of questions and answers is designed to segregate where this is important. Referring to the score sheet 108, the top three rows of triangles, connected by lines 123, 125 and 127 indicate an ability to rationalize dishonesty. Examples are marking true answers to statements such as, "There are times when the temptation to steal something becomes so strong that no average human being could resist.", and "A basically honest person can sometimes get talked into stealing from a place where they work by someone who is dishonest." The bottom two rows of triangles on the score sheet connected by lines 129 and 130 indicate how much a person "thinks" about doing something dishonest. Examples are "True" answers to statements such as, "I have at times planned to steal something but I didn't go through with it." and "If I had a dollar for every time I though about stealing something, I'd be a rich person." Interrogatories answered in such a way that triangle symbols are marked, show a state of mind in which dishonesty is acceptable. They therefore carry a rating of minus 4.

Arrow symbols 128 represent actual admissions of dishonesty, or admissions that a person would engage in a specific dishonest act if given the chance. They therefore deserve the worst dishonesty rating of minus five.

Referring to the multiple choice interrogatories on page 104 (page J on the booklet) and columns J on answer sheet 106 and score sheet 108, the symbols on the score sheet rate each of the possible answers in one of three ways. If the individual taking the test admits to having stolen money of five dollars or more, his answer would place a mark on one of the arrow symbols showing a major admission of dishonesty. If the money admitted stolen was only one dollar, the answer would fall into the tombstone symbol and represent an admission of only a minor nature. If the answer were zero, in each case the mark would fall in the circle symbol showing an honest attitude.

It will be appreciated that, during a test, the individual taking the test will not see the score sheet 108 because it is attached to and covered by the answer sheet 106.

In addition to showing honest attitude answers in the circle symbols and classifying different degrees of dishonest attitude answers by means of the other symbols, the score sheet provides additional specific information which will often be of interest to an examiner as follows. The letter "r" is placed in triangles which indicate an ability to rationalize dishonesty. The letter "t" is placed in triangles which indicate that a person thinks about doing something dishonest. The dollar sign, "$" indicates a person would steal money. "M" indicates a person would steal merchandise. "S" or "SP" indicates a person would shoplift or has shoplifted.

The tally sheet 110 provides means for automatically grading the marks entered on the score sheet by assigning different numerical values to the different-shaped symbols and deriving from the marked symbols a single numerical total score evaluating the tested individual's overall attitude toward honesty. The tally sheet assigns honesty-dishonesty numerical ratings to each of the symbols as follows:

CIRCLE SYMBOL 120—PLUS ONE
TOMBSTONE SYMBOL 122—MINUS TWO
SQUARE SYMBOL 124—MINUS THREE
TRIANGLE SYMBOL 126—MINUS FOUR
ARROW SYMBOL 128—MINUS FIVE

Thus, a predetermined value of one is assigned to honest answers and numerical values which are multiples of one are assigned to different degrees of dishonest attitudes. While the specific numerical ratings above have produced excellent results, it should be understood that the invention is not to be limited to those specific numerical ratings.

To derive a final test score from the tally sheet, all the marks for each of the different-shaped symbols on the score sheet are counted and entered in the correspondingly shaped symbols at the lower right hand corner of sheet 108. All the triangle symbols containing marks may be added and the result entered in space 132 for statistical purposes to give a numerical reading on how much a person rationalizes dishonesty and thinks about stealing. Similarly, all the major admissions of dishonesty represented by marks in arrow symbols may be collected and displayed in space 134 on the score sheet.

The total numbers of marked symbols are then transferred from the lower right hand corner of the score sheet 108 to the symbols on the tally sheet 110. The total number of honest attitude marks, in all the circle symbols on the score sheet is entered in the circle symbol 120 at the upper right hand corner of the tally sheet. To this is added the number one hundred and fifty and the subtotal is entered in space 136. Multipliers two, three, four and five assigned to the dishonest attitude symbols are then applied to the spaces within the symbols 122, 124, 126 and 128 on the tally sheet and the results of the multiplication are entered in spaces 138, 140, 142 and 144. These are assigned negative numbers by the tally sheet and are totaled in space 146. The negative total is transferred to space 148. The algebraic sum of the positive and negative numerals in spaces 136 and 148 is entered in space 150.

Applying the total score in space 150 to practical, everyday business problems, this invention is very effective in preventing and stopping employee theft and reducing turnover, and facilitates keeping conscientious personnel. Applicant's training and experience in polygraph techniques, and independent studies of this invention by outside consultants, show better than a ninety-four percent correlation with subsequent polygraph results on the same individuals. An individual's honesty rating can therefore be evaluated with better than ninety-four percent accuracy from the following score distributions:

148 and above—indicates an acceptable attitude towards honesty, can be considered a minimal security risk.

140 to 147—indicates a marginal attitude towards honesty, caution should be exercised in considering this individual for employment.

Below 139—indicates a poor attitude towards dishonesty, studies indicate that this type of attitude is similar to the attitude of individuals who have become involved in activities involving theft, and dishonesty.

It will be appreciated that the information on the tally sheet would not be available to the individual taking the test. In addition to deriving the total honesty-dishonesty score from raw data on the score sheet, numerical readouts of specific individual dishonesty attitudes and history of the individual tested can be determined for evaluation by the examiner. These include subtotals on the number of answers which rationalize dishonesty and admissions of thoughts about stealing; bad attitude answers; minor admissions of dishonesty; and major admissions of dishonesty.

While certain novel features of this invention have been shown and described and are pointed out in the annexed claims, it will be understood that various omissions, substitutions and changes in the forms and details of the invention can be made by those skilled in the art without departing from the spirit of the invention.

The embodiments of the invention in which an exclusive property or privilege is claimed are defined as follows:

1. An honesty testing and scoring evaluator for determining the attitude toward honesty of individual comprising:
   a questionnaire, and an answer and score sheet set;
   said questionnaire having a plurality of numbered interrogatories with a plurality of optional answers being printed alongside each interrogatory;
   said answer and score sheet set comprising an answer sheet overlying a score sheet, said set having means for transferring a mark placed on the answer sheet to the score sheet;
   said answer sheet having a plurality of numbered areas corresponding to said plurality of numbered interrogatories on the questionnaire, each of said areas having defined, markable spaces corresponding to said plurality of optional answers printed alongside each of said numbered interrogatoies; and
   said score sheet having a plurality of numbered areas exactly registering and corresponding with said plurality of numbered areas on the answer sheet, said score sheet having in each of its said numbered areas at least one of a plurality of symbols of different predetermined shape in exact registration with at least one of the defined, markable spaces in the corresponding area of the answer sheet, the different shaped symbols indicating different attitudes toward honesty and dishonesty on the part of the individual marking the answer sheet.

2. An honesty testing and scoring evaluator according to claim 1 with a tally sheet having means for grading said score sheet by numerically crediting the individual marking the answer sheet with marks in said symbols indicating an honest attitude and numerically debiting marks in said symbols indicating a dishonest attitude, and having means for deriving a single numerical score evaluating whether the individual has an acceptable, a marginal, or a poor attitude toward honesty.

3. An honesty testing and scoring evaluator according to claim 2 in which said symbols include at least one of a predetermined shape which is assigned a numerical value and indicates an honest attitude, and at least one of a different predetermined shape which is assigned a numerical value and indicates a dishonest attitude, and said tally sheet includes means to calculate the difference between the sums of said numerical values to evaluate the individual's overall attitude toward honesty.

4. An honesty testing and scoring evaluator according to claim 3 in which said symbols include a plurality of different predetermined shapes which indicate different degrees of dishonest attitudes, and said tally sheet assigns different numerical values to the different shaped symbols to distinguish between different degrees of dishonesty.

5. An honesty testing and scoring evaluator according to claim 4 in which the numerical values assigned by the tally sheet to the symbols indicating different degrees of dishonest attitudes are different multiples of the numerical value assigned to the symbol indicating an honest attitude.

6. An honesty testing and scoring evaluator according to claim 4 in which said plurality of different predetermined shapes of symbols identify answers which fall in the following categories of dishonesty:
   (a) a minor admissions of dishonesty;
   (b) a bad attitude toward dishonesty;
   (c) rationalizes dishonesty and thinks about stealing; and
   (d) major admissions of dishonesty.

7. An honesty testing and scoring evaluator according to claim 6 in which the numerical values assigned by the tally sheet to the symbols which indicate different degrees of dishonest attitudes are the following multiples of the numerical value assigned to the symbol indicating an honest attitude:
   for "(a)" said value is 2;
   for "(b)" said value is 3;
   for "(c)" said value is 4; and
   for "(d)" said value is 5.

8. An honesty testing and scoring evaluator according to claim 2 in which some of said interrogatories are true or false statements calling for true of false indicia on the answer sheet and others of said interrogatories are questions of the multiple choice type calling for selection of one of multiple choices on the answer sheet.

9. An honesty testing and scoring evaluator according to claim 2 in which lines on said score sheet interconnect symbols which indicate an ability to rationalize dishonesty so this attitude of the tested indivdiual can readily be evaluated by following the line and noting the symbols marked.

10. An honesty testing and scoring evaluator according to claim 2 in which lines on said score sheet interconnect symbols which indicate how much the tested individual thinks about doing something dishonest.

* * * * *

UNITED STATES PATENT AND TRADEMARK OFFICE
CERTIFICATE OF CORRECTION

PATENT NO. : 4,358,279
DATED : November 9, 1982
INVENTOR(S) : Gregory M. Lousig-Nont It is certified that error appears in the above—identified patent and that said Letters Patent is hereby corrected as shown below:

Column 2, line 4, after "sheet" insert -- set --;

Column 4, line 10, before "nature" insert -- minor --; and

Column 4, line 43, "(page J on...)" should be

-- (page J of...) --.

Signed and Sealed this

First Day of February 1983

[SEAL]

Attest:

Attesting Officer

GERALD J. MOSSINGHOFF

Commissioner of Patents and Trademarks